United States Patent [19]

Weeks

[11] Patent Number: Plant 5,858

[45] Date of Patent: Jan. 20, 1987

[54] ROSE PLANT

[76] Inventor: O. L. Weeks, 926 W. Philadelphia, Ontario, Calif. 91761

[21] Appl. No.: 698,222

[22] Filed: Feb. 4, 1985

[51] Int. Cl.[4] ..... A01H 5/00

[52] U.S. Cl. ..... Plt./11

[58] Field of Search ..... Plt./11

*Primary Examiner*—R. E. Bagwill

*Attorney, Agent, or Firm*—Vincent G. Gioia

[57] ABSTRACT

A new rose purple colored hybrid tea rose variety.

1 Drawing Figure

The present invention relates to a new and distinct variety of rose plant of the hybrid tea rose class, which was originated by my crossing as seed parent the rose known as "Louisiana" (U.S. Plant Pat. No. 3,719) and an unnamed, unpatented seedling of my creation as pollen parent. The denomination of this new rose is "Silver Spoon".

Among the novel characteristics possessed by this new variety which distinguish it from its parents and all other varieties of which I am aware are its attractive rose purple flowers borne singly, one to a stem, produced on an attractive, vigorous plant. Flowers are of good exhibition form with some contrast in tonality between petal top surface and undersurface. Asexual reproduction by budding of the new variety as performed in San Bernardino County, Calif., shows that the foregoing and other distinguishing characteristics come true to form and are established and transmitted through succeeding propagations.

The accompanying drawing shows typical specimens of the vegetative growth and flowers of the new variety in different stages of development and as depicted in color as nearly true as it is reasonably possible to make the same in a color illustration of this character.

The following is a detailed description of my new variety, with color terminology in accordance with The Royal Horticultural Society Color Chart (R.H.S.C.C.) The terminology used in color description herein refers to plate numbers in the aforementioned color chart, e.g., "75C" is plate 75C of The Royal Horticultural Society Color Chart.

Parentage: Seedling.

*Seed parent.*—"Louisiana".

*Pollen parent.*—Unnamed seedling.

Class: Hybrid tea.

The following observations are made of specimens grown outdoors in San Bernardino County, Calif., during the month of October.

FLOWER

Blooming habit: Recurrent.

A. Bud:

(1) *Size.*—Large.

(2) *Form.*—Long pointed.

(3) *Color.*—After sepals first divide, buds are reddish purple and after sepals fall, petal undersurface first seen is phlox purple, near 68C and 68D, with deeper toned petal edges near 68C on outer petals.

(4) *Sepals.*—Generally shorter than bud, but some are longer and narrower and with prickles.

(5) *Peduncle.*—Length — long. Aspect — relatively slender but sturdy. Strength — erect, strong enough to hold bloom upright. Color — near 144C but with reddish cast.

B. Bloom:

(1) *Size.*—Average size when fully expanded — about 4½ to 5 inches.

(2) *Borne.*—Singly, one to a stem.

(3) *Form.*—High centered, petals loosely roll outward as flowers open and age.

(4) *Petalage.*—Number of petals under normal conditions — about 25 to 30.

(5) *Color.*—After sepals fall and petals begin to unfurl, color of petal undersurface is near 68D. As flower opens further, color of petal top surface seems lighter than 68D, becoming near white. In the ⅓ to ½ open stage, the color contrasts attractively with deeper toned appearance of flower center where petals remain bunched. Some veining is visible, with deeper shades, e.g., 68C to 68D, appearing mainly on petal undersurface. General tonality from a distance is silvery to greyish lavender. Color at point of petal attachment is initially yellow and lightens upon aging.

C. Petals:

(1) *Texture.*—Medium.

(2) *Appearance.*—Soft with little sheen.

(3) *Form.*—Ovate with rounded edge.

(4) *Arrangement.*—Regular.

(5) *Petaloids in center.*—Few.

(6) *Persistence.*—Petals persist.

(7) *Fragrance.*—None.

(8) *Lasting quality.*—Long lasting quality on plant and 2 to 3 days as cut flower.

REPRODUCTIVE ORGANS

A. Stamens, filaments and anthers:

*Arrangement and color.*—Regularly arranged, pale yellow.

B. Pollen:

*Color.*—Yellow.

C. Styles: Uneven, short, abundant.

D. Stigmas:

*Color.*—Pale yellow.

E. Hips: None observed.

PLANT

A. Form: Upright, compact, moderately spreading.
B. Growth: Very vigorous.
*Height attained.*—About 4 to 5 feet.
C. Foliage: Compound 5 leaflets.
(1) *Size.*—Medium.
(2) *Quantity.*—Abundant.
(3) *Color.*—New foliage: Upper side — reddish purple. Under side — reddish purple. Old foliage: Upper side — near 147A to B. Under side — near 147B to C.
(4) *Shape.*—Obovate.
(5) *Texture.*—Upper side is waxy and under side is dull.
(6) *Edge. —Serrate.*
(7) *Serration.*—Regular.
(8) *Leaf stem.*—Color — near to 147C. Under side — near 147C to D.
(9) *Stipules.*—Medium.
(10) *Resistance to disease.*—Average.

D. Wood:
(1) *New wood.*—Color — near 147B to C. Bark — smooth.
(2) *Old wood.*—Color — near 147B. Bark — smooth.
E. Thorns:
(1) *Thorns.*—Quantity (main stalk) — ordinary. On laterals from stalk — few. Form — narrow, pointing downward. Length — medium. Color — brownish. Position — regular.
(2) *Prickles.*—Few to none.
F. Winter hardiness: Needs winter protection in severe climate.

I claim:

1. A new and distinct variety of rose plant of the hybrid tea rose class, substantially as shown and described, characterized particularly by rose purple flowers of good form and size borne one to a stem on an attractive, vigorous plant and having a general silvery lavender tonality from a distance.

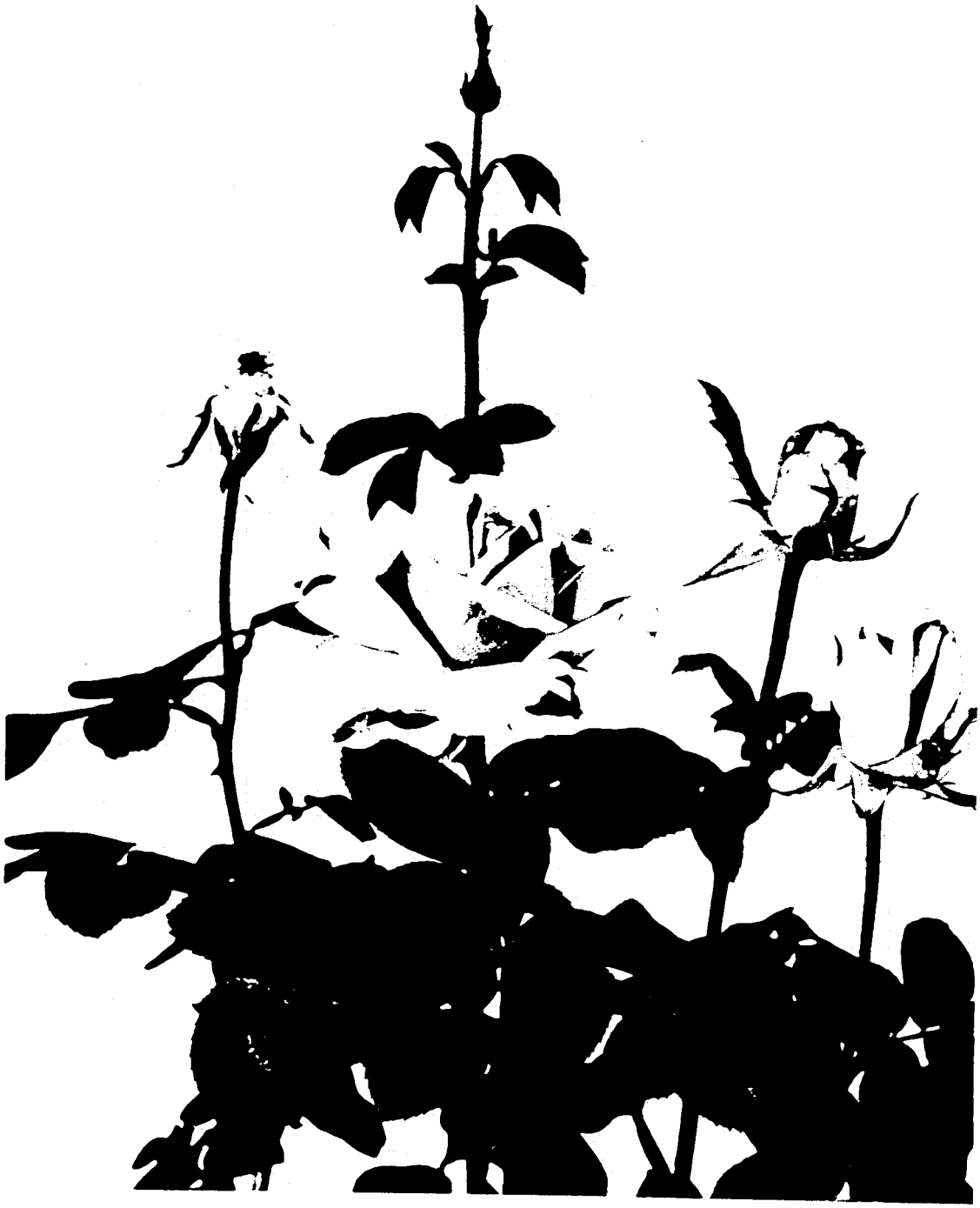

* * * * *